(12) United States Patent
Goto et al.

(10) Patent No.: US 7,030,254 B2
(45) Date of Patent: Apr. 18, 2006

(54) METHOD FOR PRODUCING PROPYLENE OXIDE

(75) Inventors: Shigeru Goto, Ichihara (JP); Koji Shinohara, Ichihara (JP); Masaaki Katao, Ichihara (JP)

(73) Assignee: Sumitomo Chemical Company, Limited, Osaka (JP)

(*) Notice: Subject to any disclaimer, the term of this patent is extended or adjusted under 35 U.S.C. 154(b) by 34 days.

(21) Appl. No.: 10/487,100

(22) PCT Filed: Aug. 13, 2002

(86) PCT No.: PCT/JP02/08238

§ 371 (c)(1),
(2), (4) Date: Feb. 19, 2004

(87) PCT Pub. No.: WO03/027086

PCT Pub. Date: Apr. 3, 2003

(65) Prior Publication Data

US 2004/0267031 A1   Dec. 30, 2004

(30) Foreign Application Priority Data

Aug. 22, 2001 (JP) ............................ 2001-251278
Aug. 22, 2001 (JP) ............................ 2001-251279

(51) Int. Cl.
  *C07D 301/19*  (2006.01)
  *C07D 301/12*  (2006.01)

(52) U.S. Cl. ........................ 549/529; 549/531
(58) Field of Classification Search ............... 549/529, 549/531
See application file for complete search history.

(56) References Cited

U.S. PATENT DOCUMENTS

| 3,350,422 A | 10/1967 | Kollar |
| 5,849,937 A * | 12/1998 | Jubin et al. ............... 549/529 |
| 6,303,800 B1 * | 10/2001 | Dingerdissen et al. ...... 549/523 |
| 6,350,888 B1 * | 2/2002 | Strebelle et al. ........... 549/529 |
| 6,646,138 B1 | 11/2003 | Oku et al. |

FOREIGN PATENT DOCUMENTS

JP    63-17873 A    1/1988
WO    WO01/05778 A1    1/2001

* cited by examiner

*Primary Examiner*—Cecilia J. Tsang
*Assistant Examiner*—Raymond Covington
(74) *Attorney, Agent, or Firm*—Sughrue Mion, PLLC

(57) ABSTRACT

A process for producing purified propylene oxide comprising:
  first to sixth steps below, and
  using heat of reaction generated in the first and/or second steps as a heat source for rectification in the fifth step and/or a heat source for rectification in the sixth step:
  first step: a step of obtaining cumene hydroperoxide trough oxidation of cumene,
  second step: a step of obtaining propylene oxide and cumyl alcohol by reacting cumene hydroperoxide with propylene in the presence of an epoxidation catalyst,
  third step: a step of separating into a fraction (2) containing crude propylene oxide and a fraction (3) containing crude propylene by subjecting an outlet liquid (1) of the second step to rectification,
  fourth step: a step of obtaining a fraction (4) containing crude propylene oxide and a fraction (6) containing cumyl alcohol by subjecting the fraction (2) to rectification,
  fifth step: a step of obtaining a fraction (7) containing purified propylene oxide by subjecting the fraction (4) to rectification, and
  sixth step: a step of obtaining a fraction (5) containing purified propylene by subjecting the fraction (3) to rectification.

3 Claims, 4 Drawing Sheets

METHOD FOR PRODUCING PROPYLENE OXIDE

TECHNICAL FIELD

The present invention relates to a process for producing propylene oxide. More particularly, the present invention relates to a process for producing purified propylene oxide, characterized by being excellent in utilization efficiency of heat of the system as a whole by utilizing efficiently reaction heat generated in a step of obtaining cumene hydroperoxide trough oxidation of cumene, and/or that generated in a step of obtaining propylene oxide and cumyl alcohol by reacting cumene hydroperoxide with propylene in the presence of an epoxidation catalyst.

PRIOR ART

A process for obtaining propylene oxide by oxidizing cumene to obtain cumene hydroperoxide and reacting the cumene hydroperoxide with propylene, is publicly known. Propylene oxide obtained is purified by subjecting to a purification step.

DISCLOSURE OF THE INVENTION

An object of the present invention is to provide a process for producing purified propylene oxide, excellent in utilization efficiency of heat of the system as a whole by utilizing efficiently heat of reaction generated in a step of obtaining cumene hydroperoxide through oxidation of cumene, and/or that generated in a step of obtaining propylene oxide and cumyl alcohol by reacting cumene hydroperoxide with propylene in the presence of an epoxidation catalyst.

Namely, the present invention relates to a process for producing purified propylene oxide which comprises first to sixth steps below, and using heat of reaction generated in the first and/or second steps as a heat source for rectification in the fifth step and/or a heat source for rectification in the sixth step:

first step: a step of obtaining cumene hydroperoxide through oxidation of cumene, second step: a step of obtaining propylene oxide and cumyl alcohol by reacting cumene hydroperoxide with propylene in the presence of an epoxidation catalyst, third step: a step of separating into a fraction (2) containing crude propylene oxide and a fraction (3) containing crude propylene by subjecting an outlet liquid (1) of the second step to rectification, fourth step: a step of obtaining a fraction (4) containing crude propylene oxide and a fraction (6) containing cumyl alcohol by subjecting the fraction (2) to rectification, fifth step: a step of obtaining a fraction (7) containing purified propylene oxide by subjecting the fraction (4) to rectification, and sixth step: a step of obtaining a fraction (5) containing purified propylene by subjecting the fraction (3) to rectification.

BEST MODE FOR CARRYING OUT THE INVENTION

Figure 1:
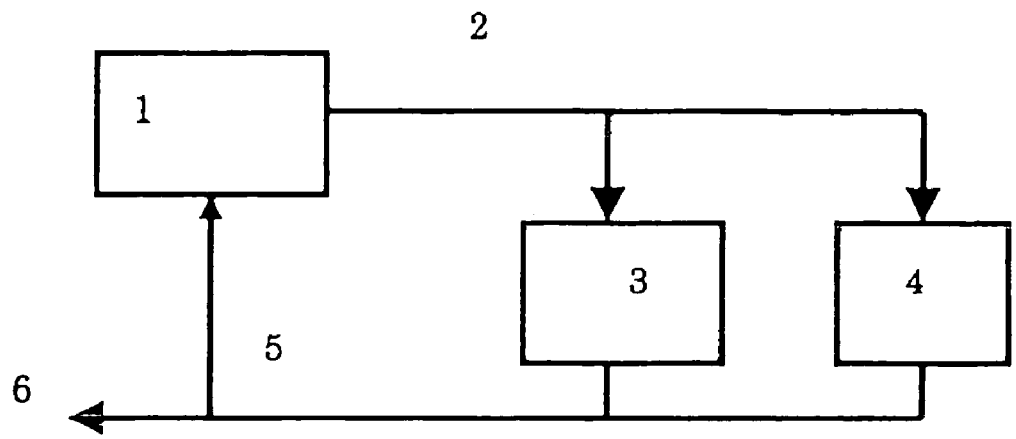
FIGS. 1 to 10 are a flow for showing one example of the invention, respectively.

The first step is a step for obtaining cumene hydroperoxide by oxidizing cumene.

The oxidation of cumene is usually conducted by auto-oxidation using an oxygen-containing gas such as air, oxygen-concentrated air or the like. Particularly, an emulsion oxidation method in an alkaline aqueous emulsion is preferable from the viewpoint of improving the yield of cumene hydroperoxide The usual reaction temperature is from 50 to 200° C., and the reaction pressure is usually from atmospheric pressure to 5 MPa. In the emulsion oxidation method, an alkali metal compound such as NaOH or KOH, alkaline earth metal compound, or alkali metal carbonate such as $Na_2CO_3$ or $NaHCO_3$, ammonia, $(NH_4)_2CO_3$ or an alkali metal ammonium carbonate or the like is used as an alkaline reagent.

The second step is a step of reacting cumene hydroperoxide obtained in the first step with propylene to obtain propylene oxide and cumyl alcohol.

The epoxidation catalyst is preferably a catalyst containing a titanium-containing silicon oxide from the viewpoint of obtaining the objective product under high yield and high selectivity. As these catalysts, so-called Ti-silica catalysts containing Ti chemically bonded to silicon oxide are preferable. For example, a catalyst prepared by supporting a Ti compound on a silica carrier, a catalyst prepared by combining a Ti compound with silicon oxide by a co-precipitation method or sol-gel method, zeolite compounds containing Ti, and the like are listed.

The epoxidation is conducted by contacting propylene and cumene hydroperoxide with the catalyst. The reaction can be carried out in a liquid phase using a solvent. The solvent must be liquid under temperature and pressure in the reaction, and substantially inert to reactants and products. The solvent may be that which is composed of a substance present in a hydroperoxide solution used. For example, when cumene hydroperoxide is a mixture with cumene which is a raw material therefor, this can be also used instead of a solvent without particularly adding a solvent. Additionally, monocyclic aromatic compounds (e.g. benzene, toluene, chlorobenzene, orthodichlorobenzene), and alkanes (e.g. octane, decane, dodecane) and the like are listed as useful solvents.

The epoxidation temperature is usually from 0 to 200° C., and preferably from 25 to 200° C. The pressure may be at a level sufficient to keep the reaction mixture in a liquid condition. In general, the pressure is advantageously from 100 to 10000 kPa.

The epoxidation can be carried out advantageously using a catalyst in the form of a slurry or fixed bed. In the case of a large scale industrial operation, a fixed bed is preferably used. The epoxidation can be conducted by a batch-wise method, semi-continuous method, continuous method or the like. When liquid containing raw materials for reaction is passed through a fixed bed, a liquid-like mixture discharged from a reaction region does not contain a catalyst at all or contains substantially no catalyst.

The third step is a step for separating into the fraction (2) containing crude propylene oxide and the fraction (3) containing crude propylene by subjecting an outlet liquid (1) of the second step to rectification.

A specified example of this step includes a method of subjecting the outlet liquid (1) from the second step to distillation, and recovering crude propylene (3) containing unreacted propylene from the top of a distillation column and the fraction (2) containing crude propylene oxide and cumyl alcohol from the bottom of the distillation column.

The fourth step is a step for obtaining the fraction (4) containing crude propylene oxide and the fraction (6) containing cumyl alcohol by subjecting the fraction (2) to rectification.

Specified examples of this step include a method of subjecting the fraction (2) containing crude propylene oxide from the third step to distillation, and recovering the fraction (4) containing crude propylene oxide from the top of a distillation column, and the fraction (6) containing cumyl alcohol from the bottom of the distillation column.

The fifth step is a step for obtaining a fraction (7) containing purified propylene oxide by subjecting the fraction (4) to rectification.

A specified example of this step includes a method of subjecting the fraction (4) containing crude propyleneoxide from the fourth step to distillation, and obtaining the fraction (7) containing purified propylene oxide by removing a light fraction and a heavy fraction. As the distillation method, a method of using a plurality of distillation columns and a method of adopting an extractive distillation.

The sixth step is a step for obtaining the fraction (5) containing purified propylene by subjecting the fraction (3) to rectification.

A specified example of this step includes a method of subjecting the fraction (3) containing crude propylene of the third step to distillation for separating impurities such as propane, ethane, ethylene, methane and the like contained in propylene industrially applicable therefrom, and obtaining the fraction (5) containing purified propylene.

The utmost characteristic of the present invention is to use heat of reaction generated in the first and/or second steps as a heat source for rectification in the fifth step and/or a heat source for rectification in the sixth step. As a method of using the heat of reaction as a heat resource for rectification, the following methods can be illustrated.

A recovering method of heat of reaction generated in the first step includes a direct method in which a reaction liquid is directly heat-exchanged with a process liquid to be utilized, and an indirect method in which a reaction liquid is heat-exchanged with a process liquid to be utilized through a heat medium different from the process liquid. In the former, it is possible to attain thermal exchange in good efficiency because of no heat medium, and on the other hand, in the latter, it is possible to attain thermal exchange with a simple installation by using a heat medium of high stability.

Further, utilization of heat accompanying a reaction such as heat of reaction generated in the first step and/or second step is different in a temperature level capable of being thermally utilized because a reaction temperature is changed depending on operation conditions such as a load and the like.

Therefore, it is possible to provide a process for producing purified propylene oxide, characterized by being excellent in utilization efficiency of heat of the system as a whole by incorporating a utilization of heat which is not affected on change of operation conditions.

For attaining a stable heat utilization even if operation conditions move, it is important that the amount of heat consumed is larger than that of the heat of reaction, and a temperature difference between an applicable temperature and reaction temperature is 10° C. or more, desirably 20° C. or more. In other words, a distillation column having a large amount of heat consumption and a distillation column in which the boiling point of a processed fluid is low, are most proper.

Because boiling points of propylene oxide and propylene among processed fluids areas low as 34° C. and −48° C., respectively, it is effective for improvement of utilization efficiency of heat of the system as a whole to conduct a heat utilization in the fifth and sixth steps in which purification operations of both fluids are carried out.

As a method of heat utilization in the fifth and sixth steps of the heat of the reaction of the first and/or second steps, a method of conducting a heat utilization by circulating a reaction liquid from the first and/or second steps to the fifth and sixth steps; a method of conducting a heat utilization by circulating a liquid to be processed in the fifth and sixth steps to the first and/or second steps; a method of circulating a heating medium such as hot water between the first and/or second steps, and the fifth and sixth steps; and a method of generating steam with the heat of reaction in the first and/or second steps and using the steam in the fifth and sixth steps, are exemplified.

Examples of the present invention are explained using drawings below.

In FIG. 1, a heat exchange is carried out by passing a hot oxidation liquid 2 from the oxidation reactor 1 in the first step through a heat exchanger 3 of the fifth step and a heat exchanger 4 of the sixth step. A cold oxidation liquid 5 passed through the heat exchanger is supplied to an epoxidation reactor 6 and a part thereof returns to the oxidation reactor 1. Herein, the oxidation reactor 1 may be a single reactor or multi-stages reactor, and can be selected properly.

Figure 2:
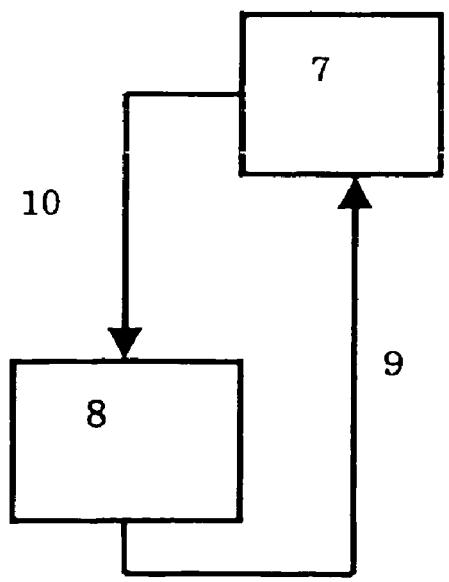
Figure 3:
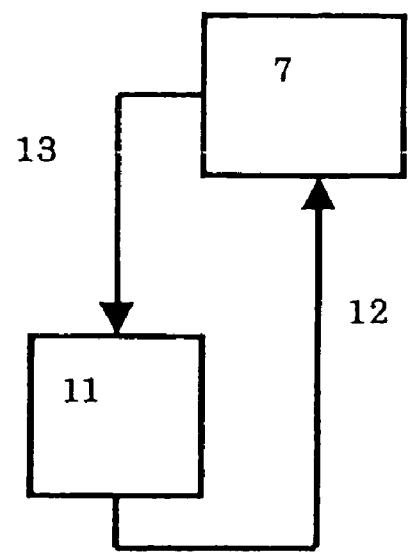
Figure 4:
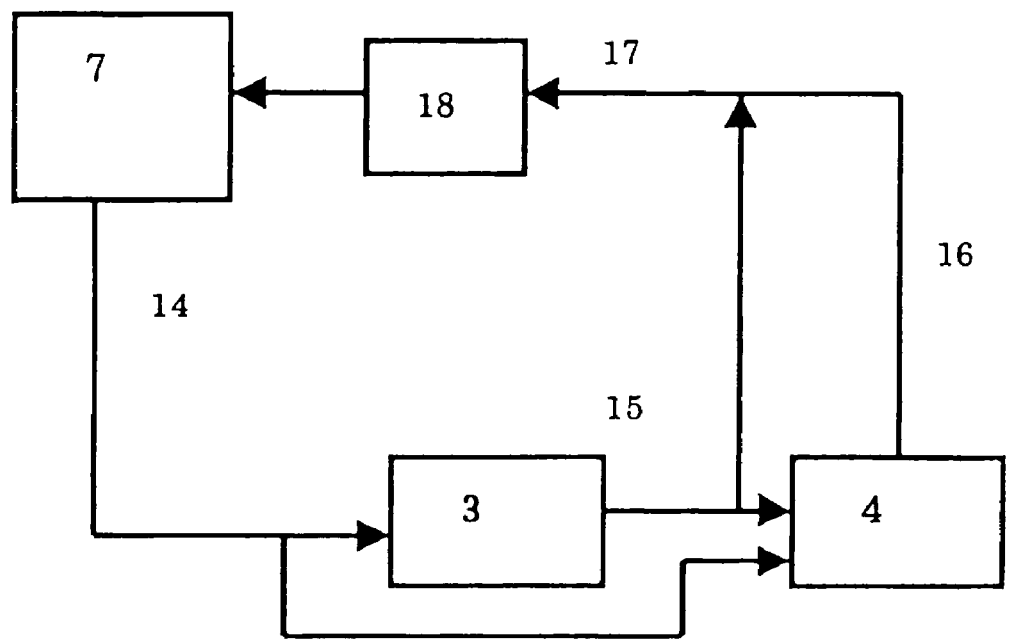
Figure 5:
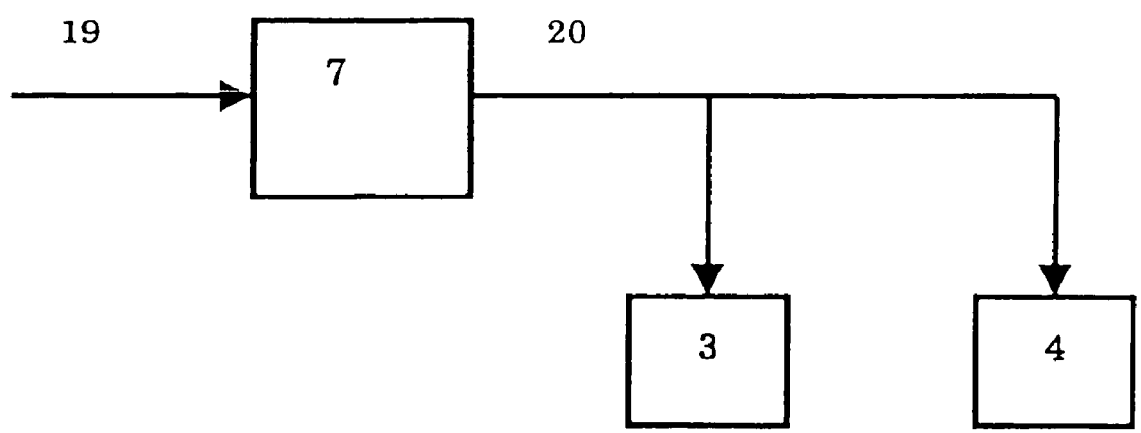

In FIGS. 2 and 3, a cold liquid 9 to be processed in the fifth step and cold liquid 12 to be processed in the sixth step are respectively heated by passing through a heat exchanger 7 to obtain a hot liquid 10 to be processed in the fifth step and a hot liquid 13 to be processed in the sixth step, respectively, and these are supplied to a distillation column 8 of the fifth step and a distillation column 11 of the sixth step, respectively. In FIG. 4, a hot heating medium 14 heated by passing through the heat exchanger 7 of the oxidation reactor of the first step, passes through a heat exchanger 3 of the fifth step and a heat exchanger 4 of the sixth step. Cold heating media 15 and 16 which have passed through each of the heat exchangers, are heated again by the heat exchanger 7 of the oxidation reactor, but, as shown in the Fig., a heat storage tank 18 may be installed there before. Further, as shown the Fig., a part or whole of the heating medium 15, depending on the temperature thereof, may be supplied to the heat exchanger 4 of the sixth step. Furthermore, as another embodiment, it is possible to allow the hot heating medium 14 to pass through only the heat exchanger 3 of the fifth step or the heat exchanger 4 of the sixth step. In FIG. 5, water 19 supplied to a boiler is changed to steam 20 by heating with the heat exchanger 7 of the oxidation reactor in the first step, and is sent to the heat exchanger 3 of the fifth step and the heat exchanger 4 of the sixth step as a heating medium.

Figure 6:
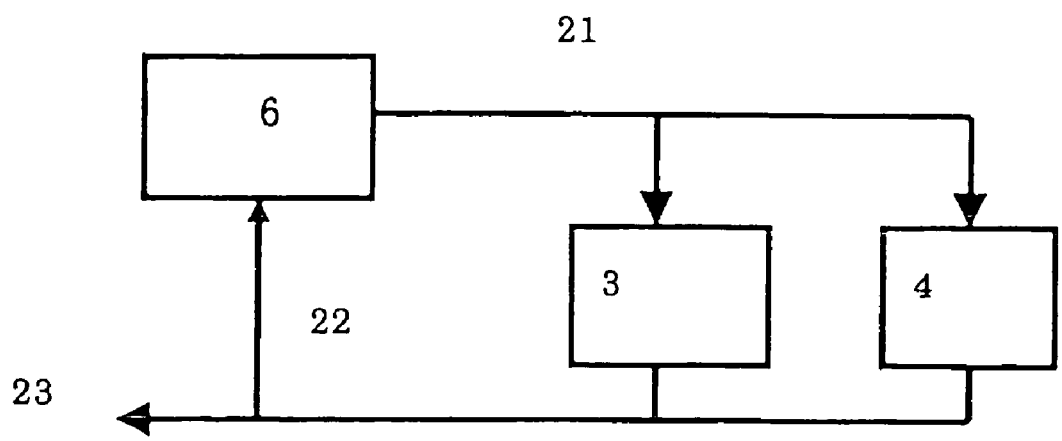

In FIG. 6, a heat exchange is carried out by allowing a hot epoxidation liquid 21 from the epoxidation reactor 6 of the second step to pass through the heat exchanger 3 of the fifth step and the heat exchanger 4 of the sixth step. A cold epoxidation liquid 22 which has passed through the heat exchanger, is supplied to a separation step 23 in the third step. Further, a part thereof may be returned to the epoxidation reactor 6. Herein, the epoxidation reactor 6 may be a single reactor or multi-stages reactor, and can be selected properly.

Figure 7:
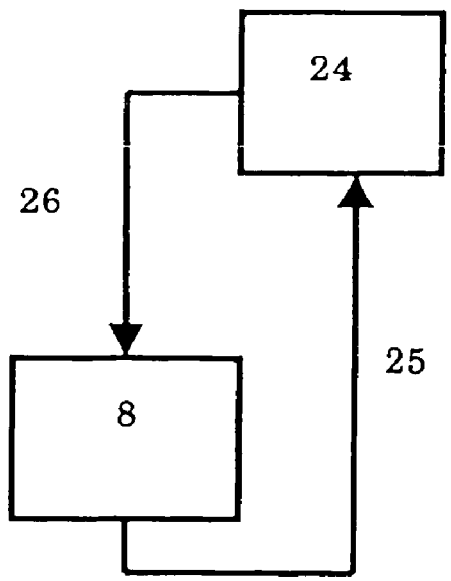
Figure 8:
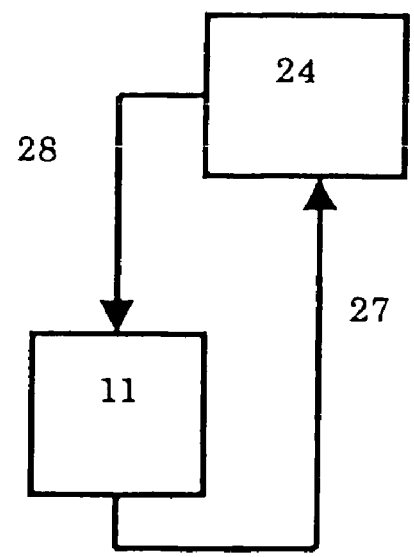
Figure 9:
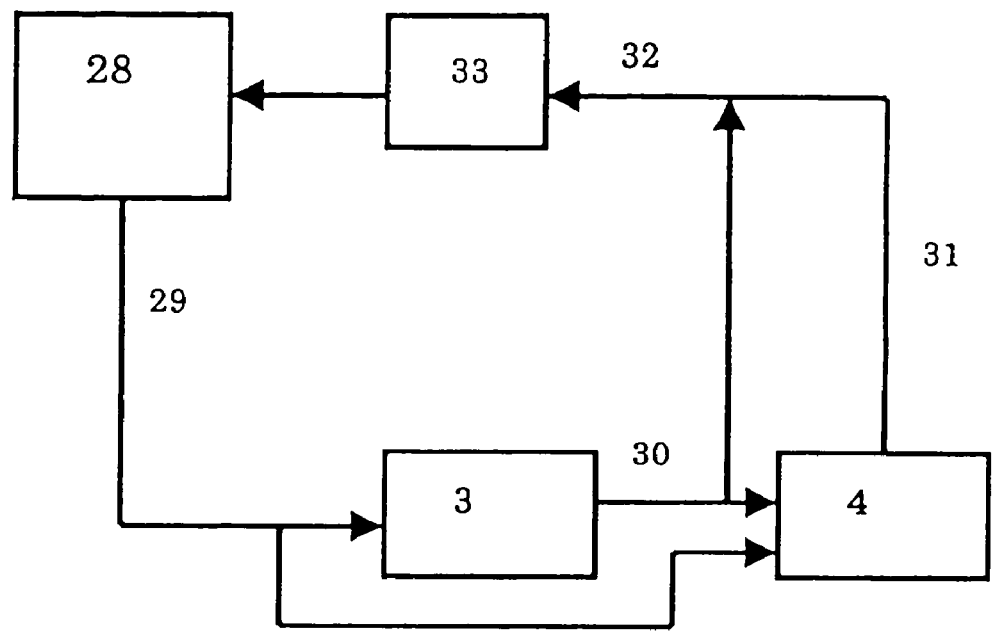

In FIGS. 7 and 8, a cold liquid 25 to be processed in the fifth step and cold liquid 27 to be processed in the sixth step are respectively heated by passing through a heat exchanger 24 of the epoxidation reactor to obtain a hot liquid 26 to be processed in the fifth step and a hot liquid 28 to be processed in the sixth step, respectively, and these are supplied to a distillation column 8 of the fifth step and a distillation column 11 of the sixth step, respectively. In FIG. 9, a hot heating medium 29 heated by passing through the heat exchanger 28 of the epoxidation reactor in the second step, pass through a heat exchanger 3 of the fifth step and a heat exchanger 4 of the sixth step.

Heating media 30 and 31 passing through each of the heat exchangers, are heated again by the heat exchanger 28 of the epoxidation reactor, but, as shown in the Fig., a heat storage tank 33 may be installed there before.

Figure 10:
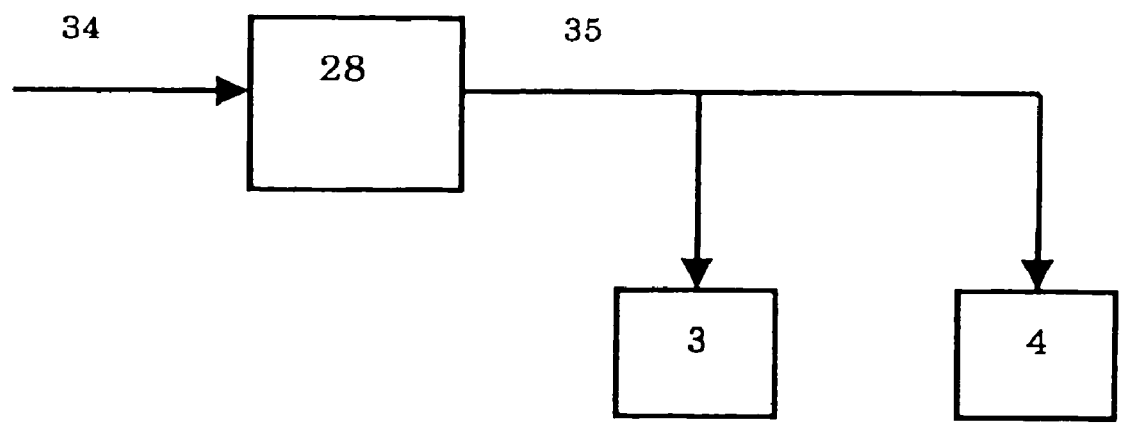

Further, as shown the Fig., a part or whole of a heating medium 30, depending on the temperature thereof, may be supplied to the heat exchanger 4 of the sixth step. Furthermore, as another embodiment, it is possible to allow the hot heating medium 29 to pass through only the heat exchanger 3 of the fifth step or only the heat exchanger 4 of the sixth step. In FIG. 10, water 34 supplied to a boiler is changed to steam 35 by heating with the heat exchanger 28 of the oxidation reactor in the first step, and the steam is sent to the heat exchanger 3 of the fifth step and the heat exchanger 4 of the sixth step as a heating medium.

Besides, in the drawings, embodiments of which the heat of reaction generated in the first step and that in the second step are separately utilized as heat sources of rectifications of the fifth and sixth steps, were shown, but it is possible to use the heat generated in both of the first and second steps as heat sources for both of the fifth and sixth steps, namely, for example, to utilize separately the heat of reaction generated in the first step and that in the second step as a heat source for rectification in the fifth step and as that in the sixth step, respectively, and further, to also utilize those together as a heat source for rectification in the fifth step and as that in the sixth step.

INDUSTRIAL APPLICABILITY

According to the present invention, a process for producing purified propylene oxide, excellent in utilization efficiency of heat of the system as a whole by utilizing efficiently heat of reaction generated in the first and/or second steps, can be provided.

The invention claimed is:

1. A process for producing purified propylene oxide comprising:

first to sixth steps below, and using heat of reaction generated in the first and/or second steps as a heat source for rectification in the fifth step and/or a heat source for rectification in the sixth step:

first step: a step of obtaining cumene hydroperoxide through oxidation of cumene at a temperature of from 50 to 200° C., second step: a step of obtaining propylene oxide and cumyl alcohol by reacting cumene hydroperoxide with propylene at a temperature of from 0 to 200° C. in the presence of an epoxidation catalyst, third step: a step of separating into a fraction (2) containing crude propylene oxide and a fraction (3) containing crude propylene by subjecting an outlet liquid (1) of the second step to rectification, fourth step: a step of obtaining a fraction (4) containing crude propylene oxide and a fraction (6) containing cumyl alcohol by subjecting the fraction (2) to rectification, fifth step: a step of obtaining a fraction (7) containing purified propylene oxide by subjecting the fraction (4) to rectification, and sixth step: a step of obtaining a fraction (5) containing purified propylene by subjecting the fraction (3) to rectification, wherein the reaction temperature in the first and/or second steps is higher by 10° C. or more than the temperature of a heat source for rectification in the fifth and/or sixth steps.

2. The process according to claim 1, wherein the reaction temperature in the first and/or second steps is higher by 20° C. or more than the rectification temperature.

3. The process according to claim 1, wherein the epoxidation catalyst is a catalyst containing a titanium-containing silicone oxide.

* * * * *